US005569968A

United States Patent [19]
Lal et al.

[11] Patent Number: 5,569,968
[45] Date of Patent: Oct. 29, 1996

[54] MICROFABRICATED ACOUSTIC SOURCE AND RECEIVER

[75] Inventors: Amit Lal; Richard M. White, both of Berkeley, Calif.

[73] Assignee: The Regents Of The University Of California, Oakland, Calif.

[21] Appl. No.: 306,843

[22] Filed: Sep. 14, 1994

Related U.S. Application Data

[63] Continuation of Ser. No. 72,294, Jun. 4, 1993, abandoned.
[51] Int. Cl.$^6$ ........................................ H01L 41/08
[52] U.S. Cl. ......................... 310/322; 310/311; 310/334
[58] Field of Search ............................ 310/313 R, 311, 310/321, 322, 328, 334; 381/173, 113, 191, 181; 367/181; 322/334

[56] References Cited

U.S. PATENT DOCUMENTS

| | | | |
|---|---|---|---|
| 4,764,244 | 8/1988 | Chitty et al. | 156/630 |
| 4,783,821 | 11/1988 | Muller et al. | 381/173 |
| 5,006,749 | 4/1991 | White | 310/323 |
| 5,025,346 | 6/1991 | Tang et al. | 361/83 |
| 5,049,775 | 9/1991 | Smits | 310/328 |
| 5,129,286 | 7/1992 | White et al. | 310/313 R |
| 5,162,691 | 11/1992 | Mariani et al. | 310/321 |
| 5,189,914 | 3/1993 | White et al. | 73/599 |
| 5,195,374 | 3/1993 | Parsons et al. | 73/704 |
| 5,248,912 | 9/1993 | Zdeblick et al. | 310/332 |
| 5,336,062 | 8/1994 | Richter | 417/413 A |
| 5,339,289 | 8/1994 | Erickson | 367/149 |
| 5,344,117 | 9/1994 | Trah et al. | 251/11 |

OTHER PUBLICATIONS

E. Graf et al., "Silicon membrane condenser microphone with integrated field-effect transistor," *Sensors and Actuators A*, vol. 37–38 (Jun.–Aug. 1993), pp. 708–711.

Kim, E.S. et al., "Improved ICI-compatible piezoelectric Microphone and CMOS process," *Transducers*, 1991, San Francisco.

Kim, E.S. et al., "IC-processed Piezoelectric Microphone," *IEEE Electron Device Lett.*, vol. EDL–8, Oct. 1987, pp. 467–468.

Donk, et al., "Preliminary results of a silicon condenser microphone with internal feedback," *Transducers*, 1991, San Francisco.

Bearden, et al., *Optics Lett.*, vol. 18, No. 3, Feb. '93, pp. 238–240.

Junger, et al., *Sound Structures and Their Interaction*, pp. 235–272, MIT Press, 1986.

Kaliski, S., et al., *Vibrations and Waves*, 1992, pp. 313–325.

*Primary Examiner*—Thomas M. Dougherty
*Attorney, Agent, or Firm*—Fish & Richardson P.C.

[57] ABSTRACT

A microstructure that may be used as an acoustic source or receiver. It comprises a substrate having a thicker section and a thinner section, supporting a membrane. A window is formed in the thinner section. Means are provided for inputting or sensing mechanical energy in the substrate and membrane. The microstructure allows for the design of complex mechanical frequency responses for at least partly mechanical signal processing.

39 Claims, 12 Drawing Sheets

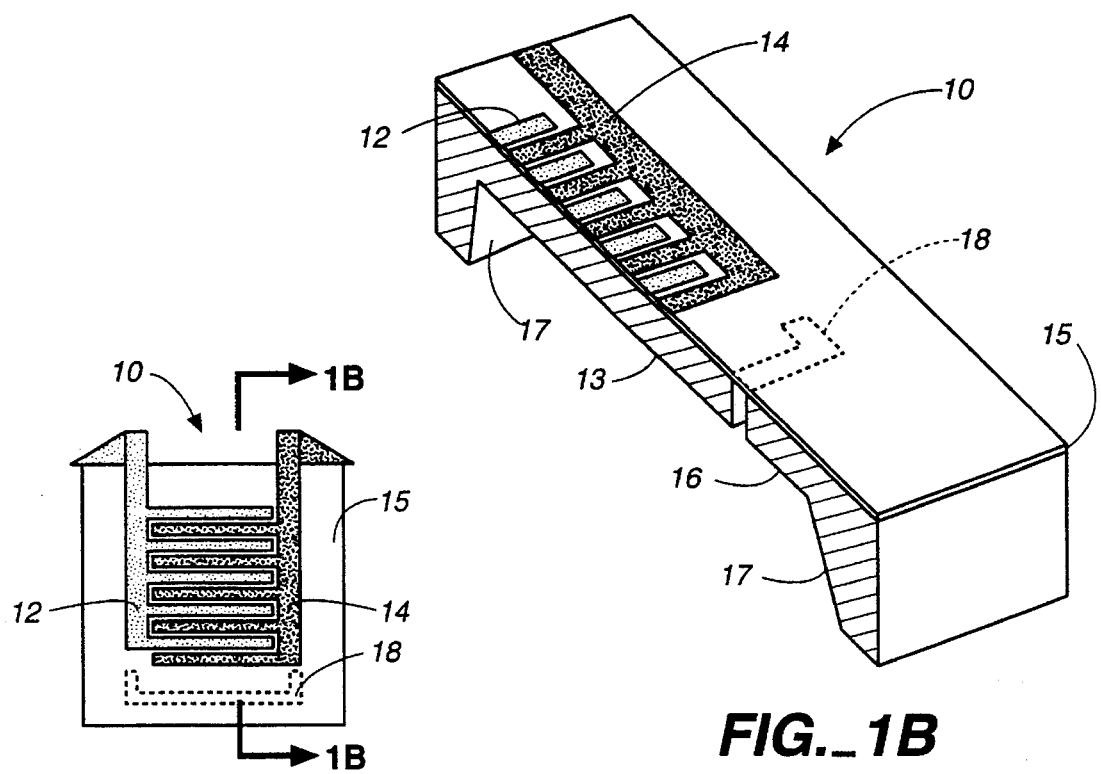
FIG._1A
FIG._1B
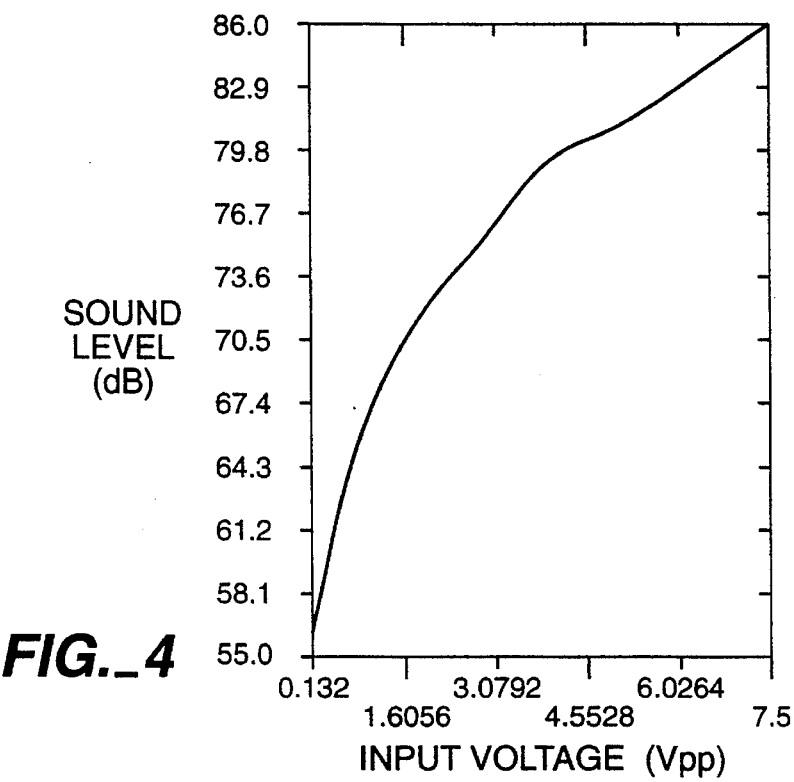
FIG._4

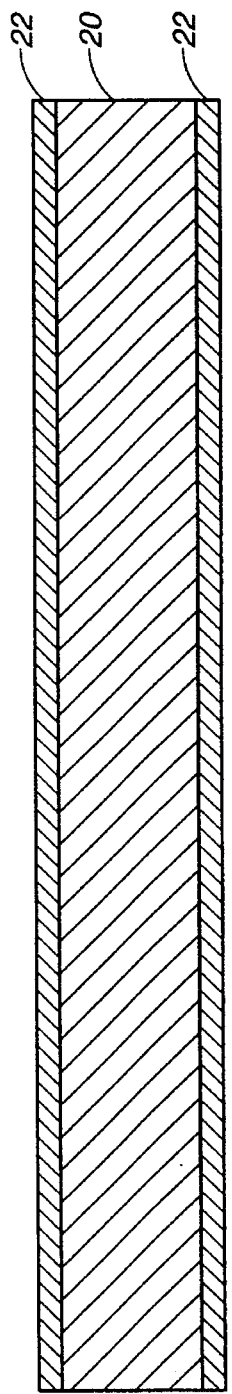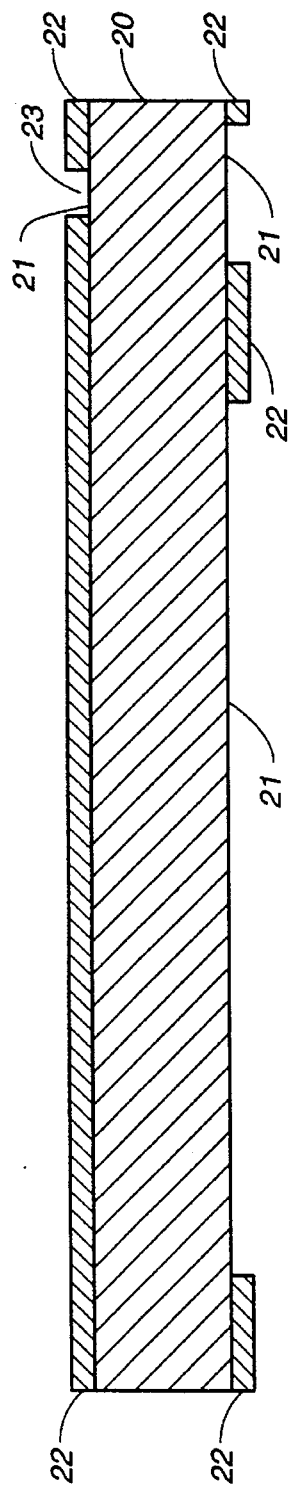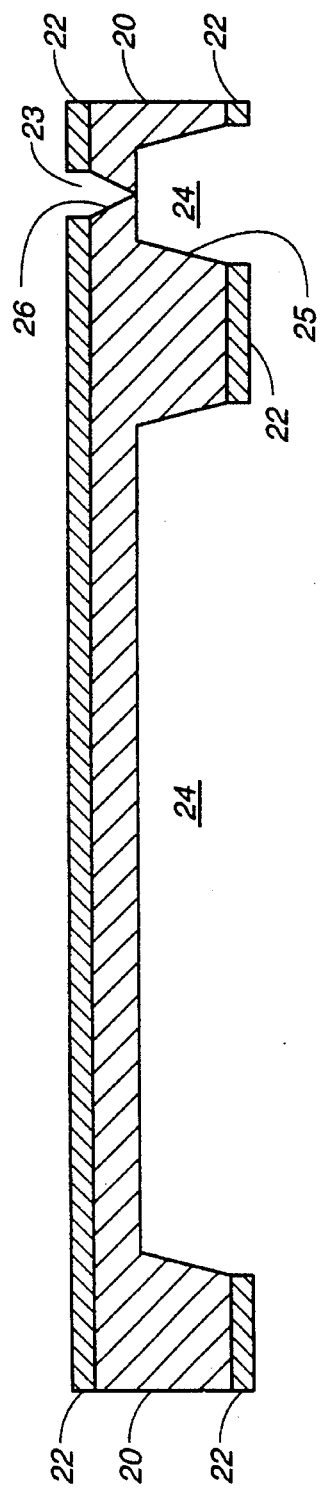
FIG._2A  FIG._2B  FIG._2C

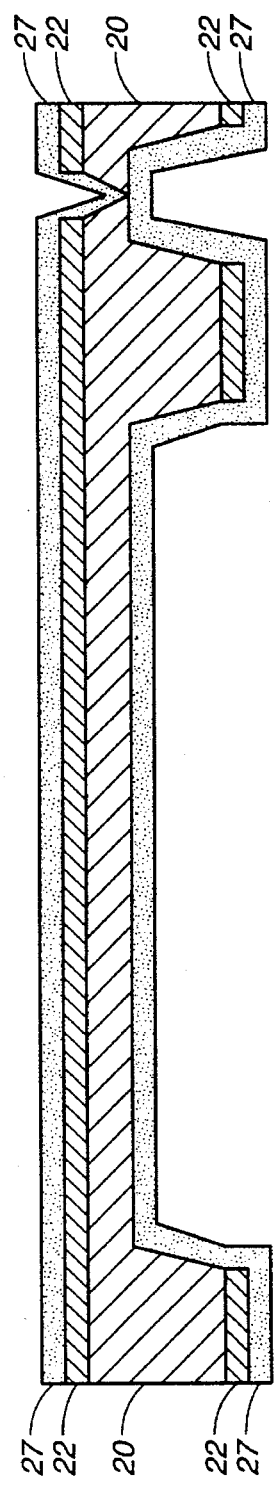
FIG._2D
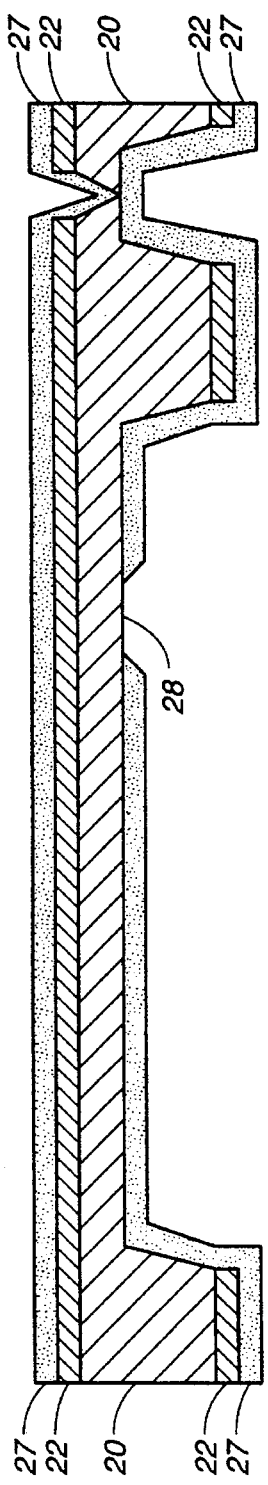
FIG._2E
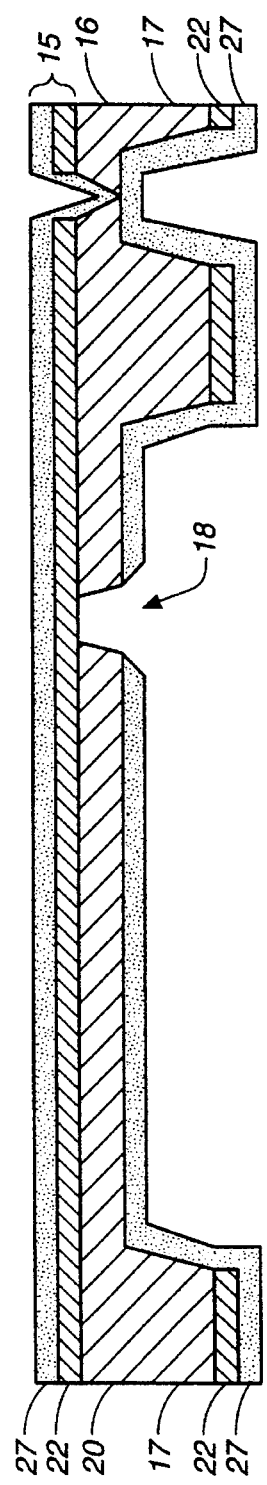
FIG._2F

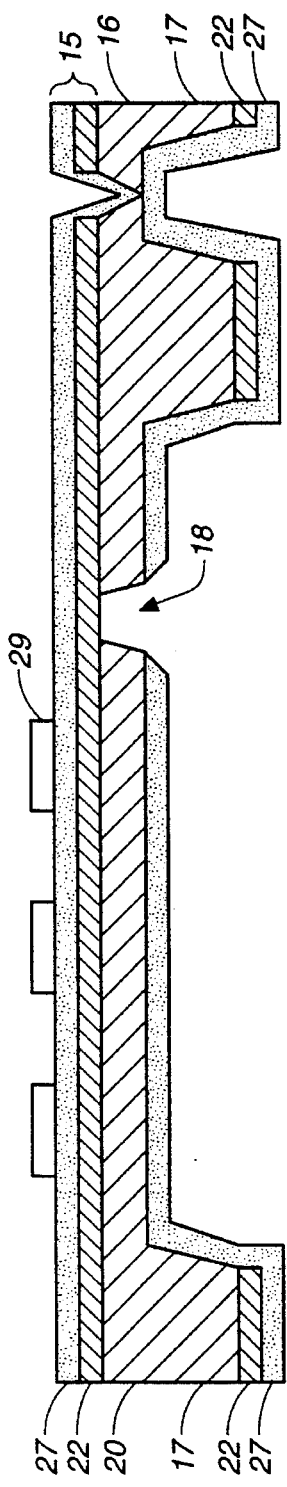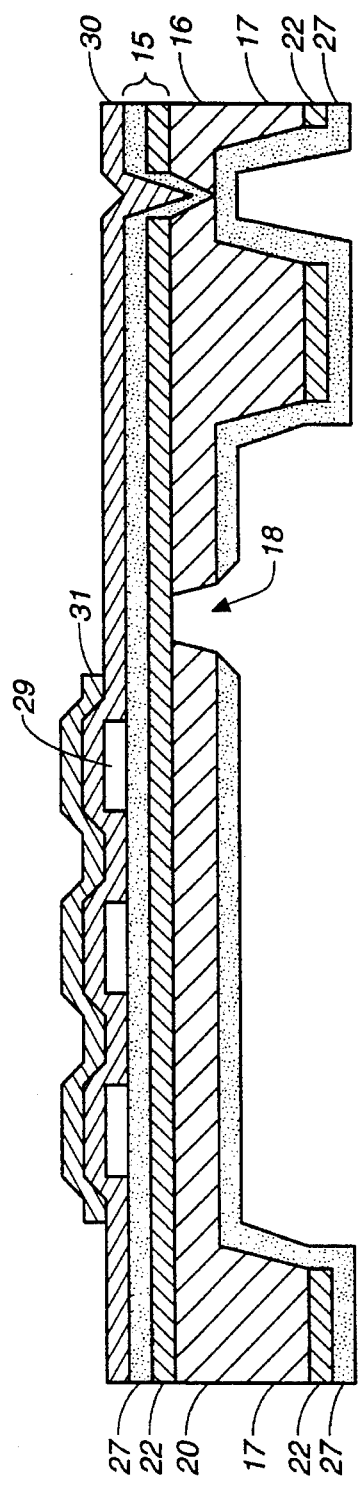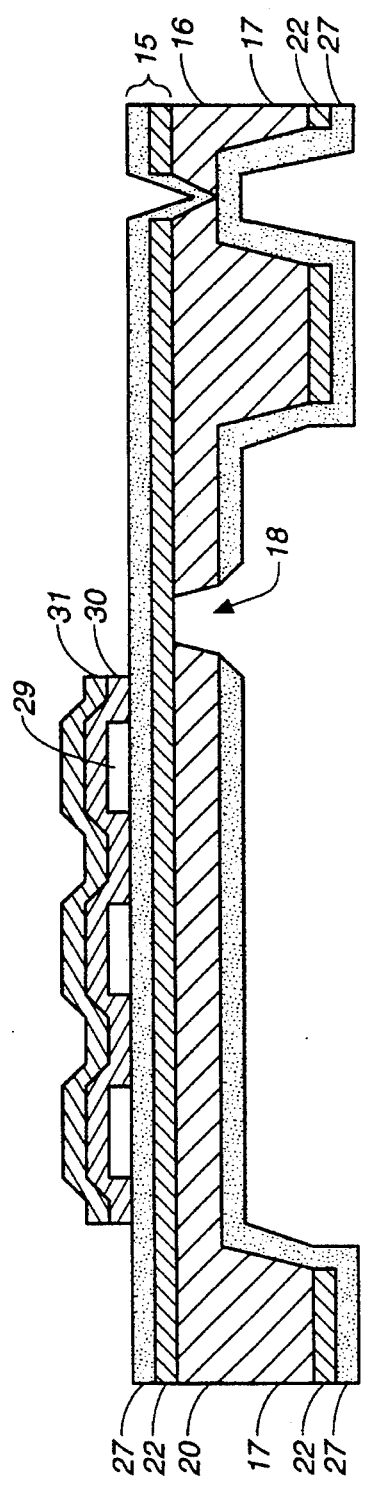

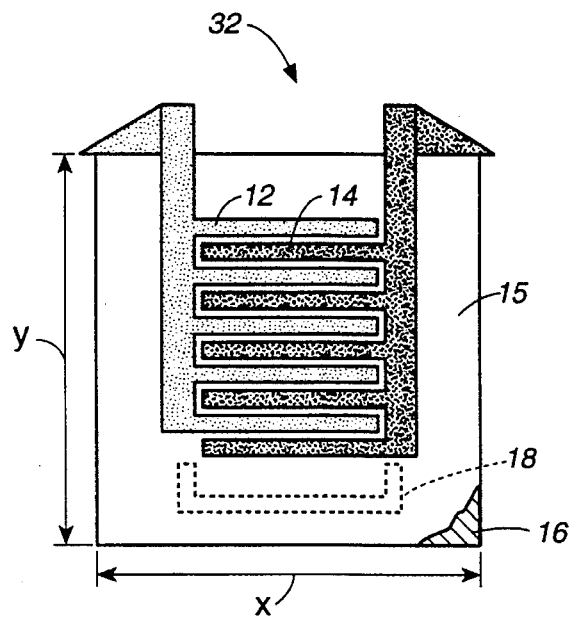
FIG._3A
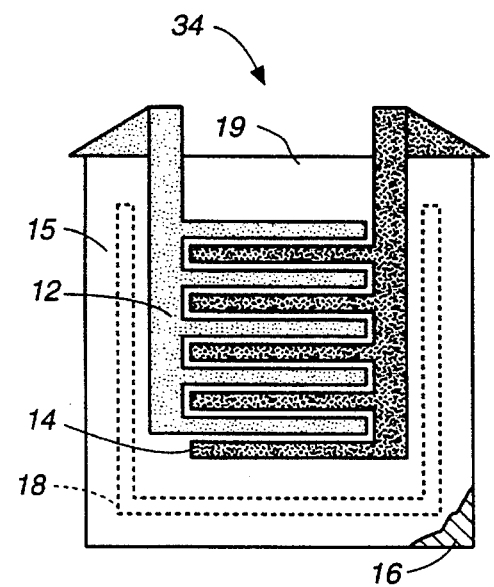
FIG._3B
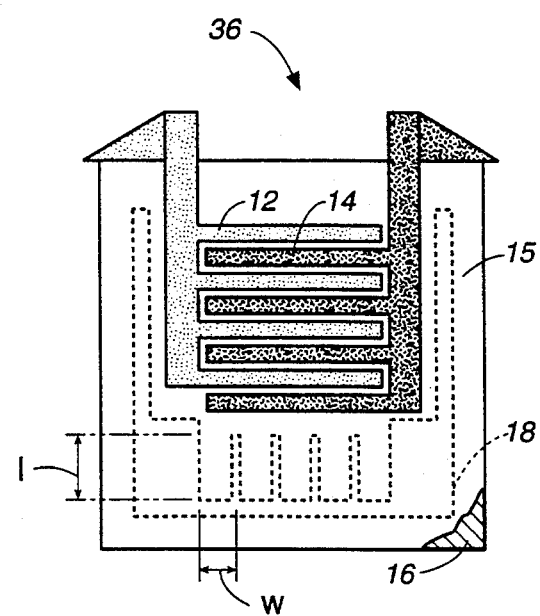
FIG._3C
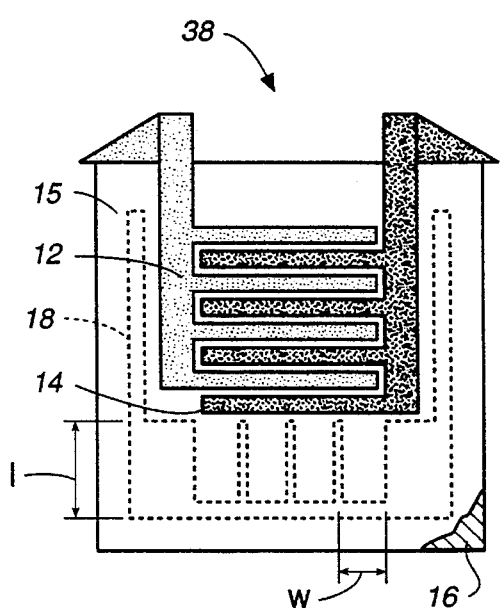
FIG._3D

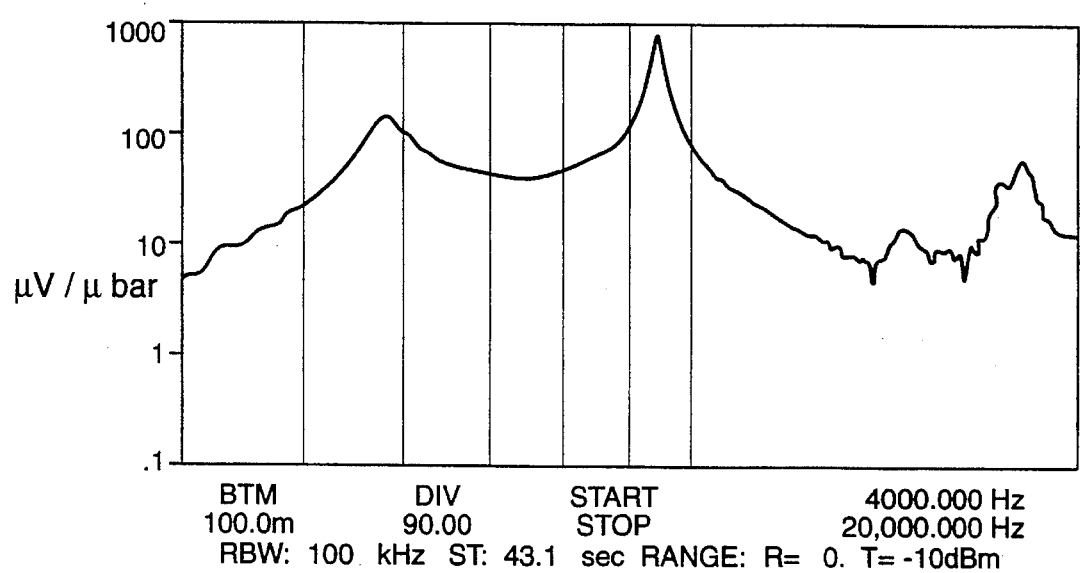
FIG._5A
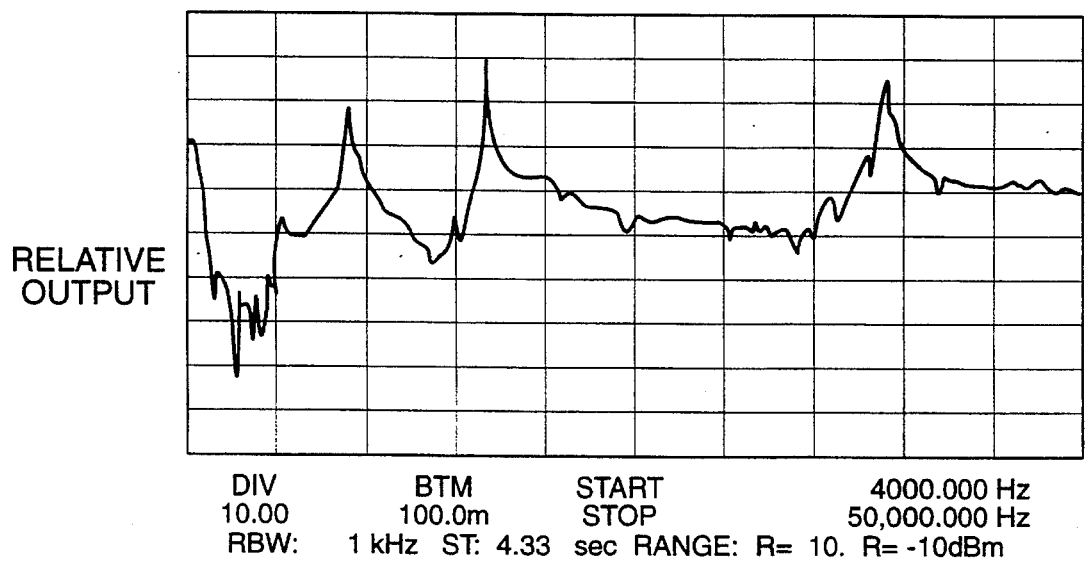
FIG._5B

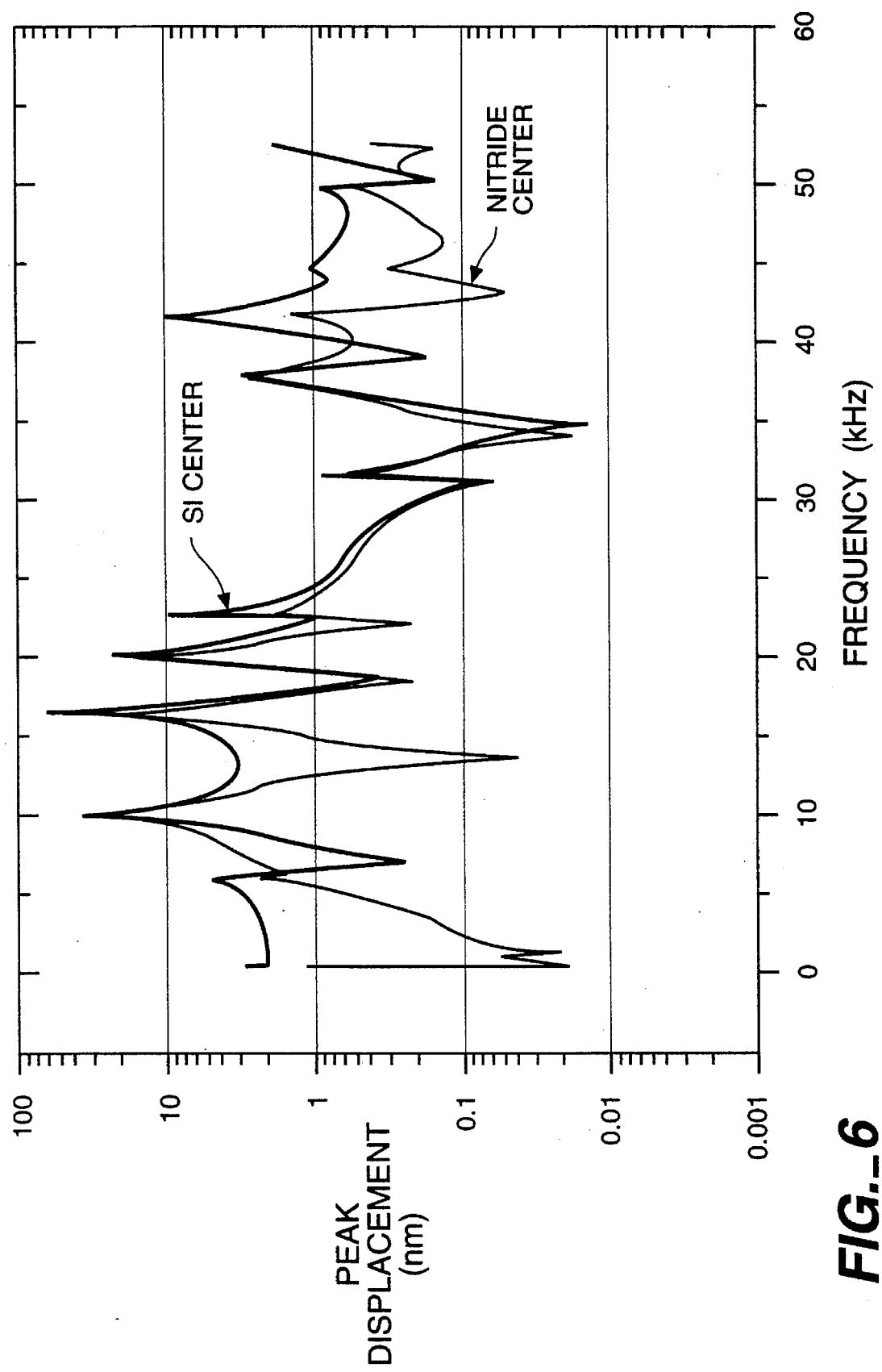
FIG._6

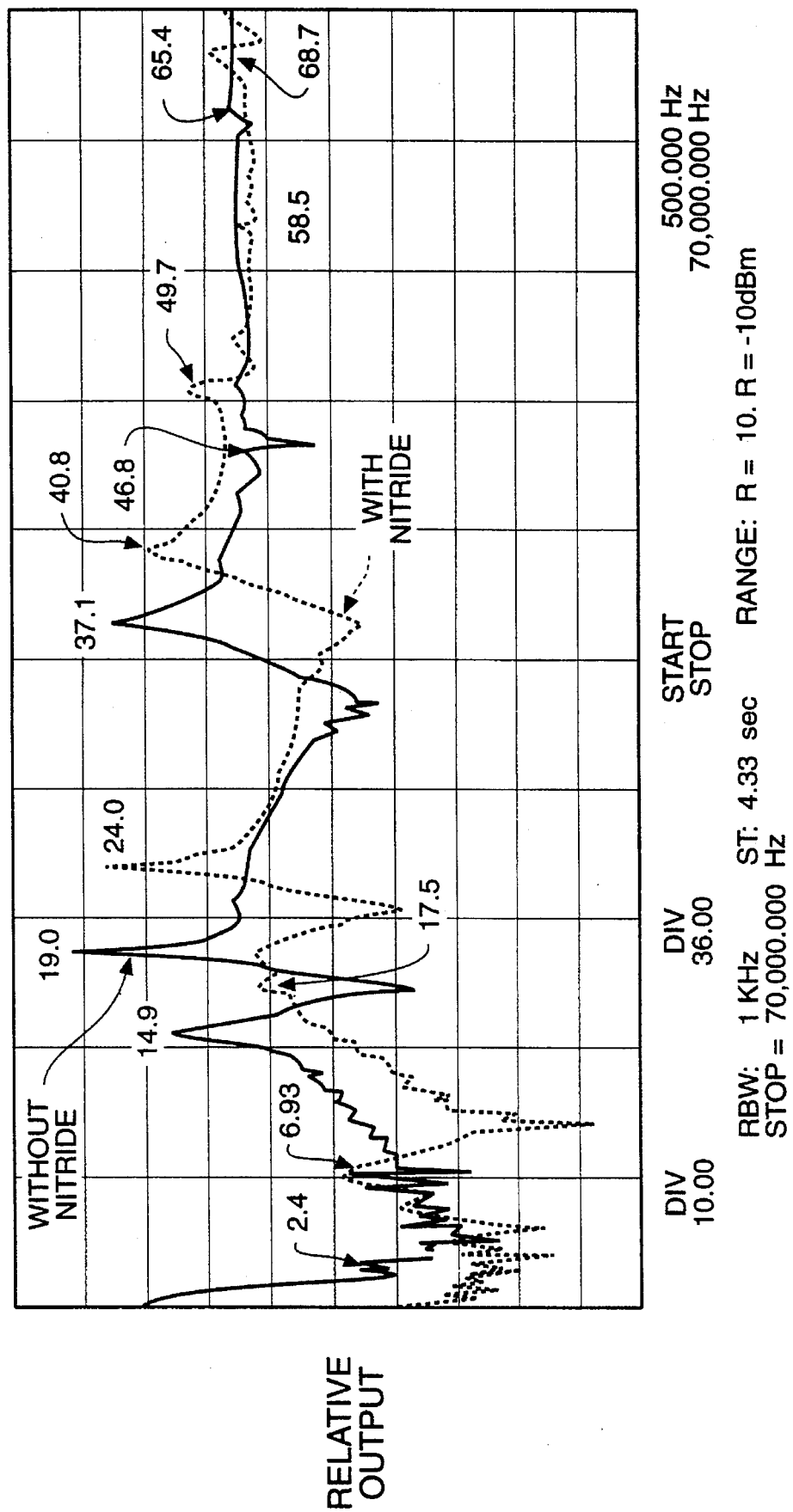
FIG._7

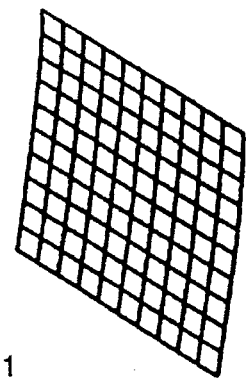
MODE 1
Frequency = 2059.8
Air wavelength = 16cm
FIG._8A
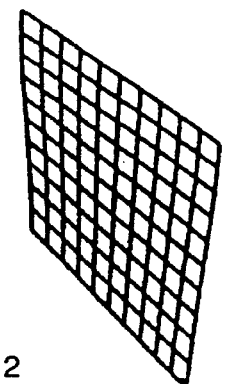
MODE 2
Frequency = 4876
Air wavelength = 6.77cm
FIG._8B
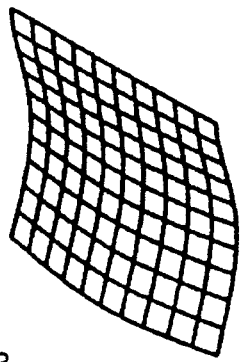
MODE 3
Frequency = 12562
Air wavelength = 2.63cm
FIG._8C
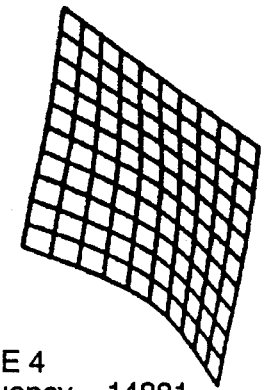
MODE 4
Frequency = 14881
Air wavelength = 2.21cm
Measured mode frequency > 14.9kHz
FIG._8D
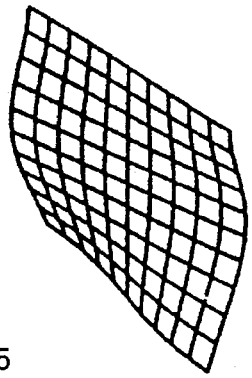
MODE 5
Frequency = 17935
Air wavelength = 1.84cm
Measured mode frequency > 19.0kHz
FIG._8E
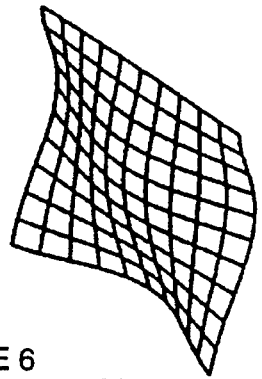
MODE 6
Frequency = 30607
Air wavelength = 1.08cm
FIG._8F

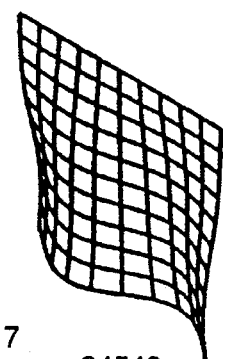
MODE 7
Frequency = 34549
Air wavelength = 0.95cm
FIG._8G
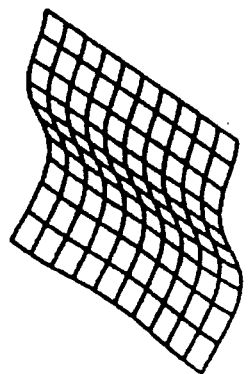
MODE 8
Frequency = 36367
Air wavelength = 0.91cm
Measured mode frequency > 37.1kHz
FIG._8H
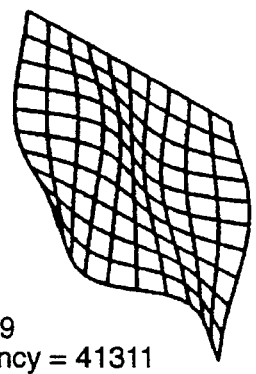
MODE 9
Frequency = 41311
Air wavelength = 0.8cm
FIG._8I
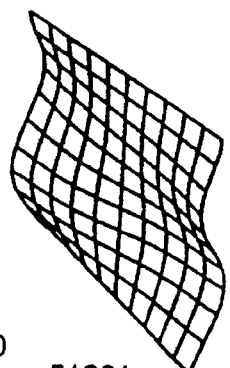
MODE 10
Frequency = 51261
Air wavelength = 0.64cm
FIG._8J
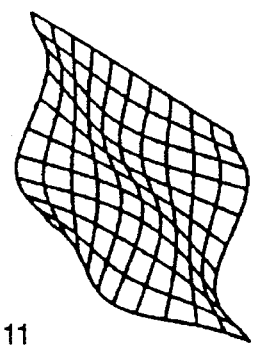
MODE 11
Frequency = 55360
Air wavelength = 0.596cm
FIG._8K
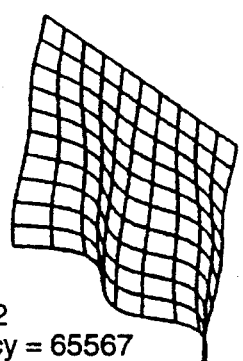
MODE 12
Frequency = 65567
Air wavelength = 0.5cm
Measured mode frequency > 65.4kHz
FIG._8L

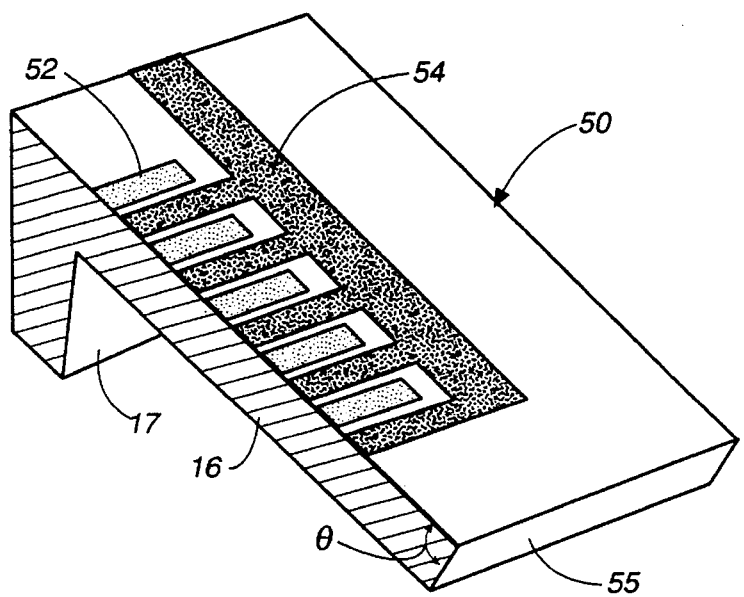
FIG._9A
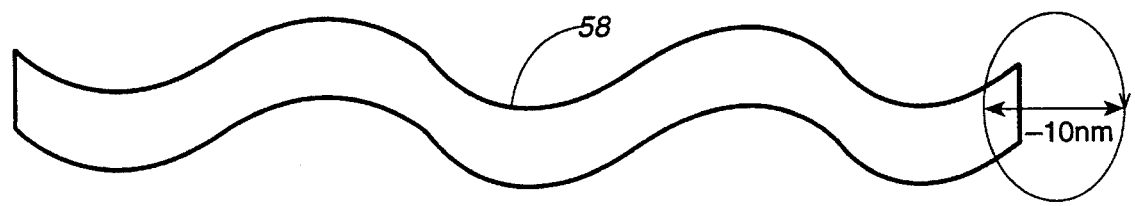
FIG._9B
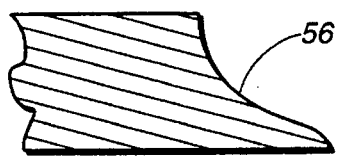
FIG._9C

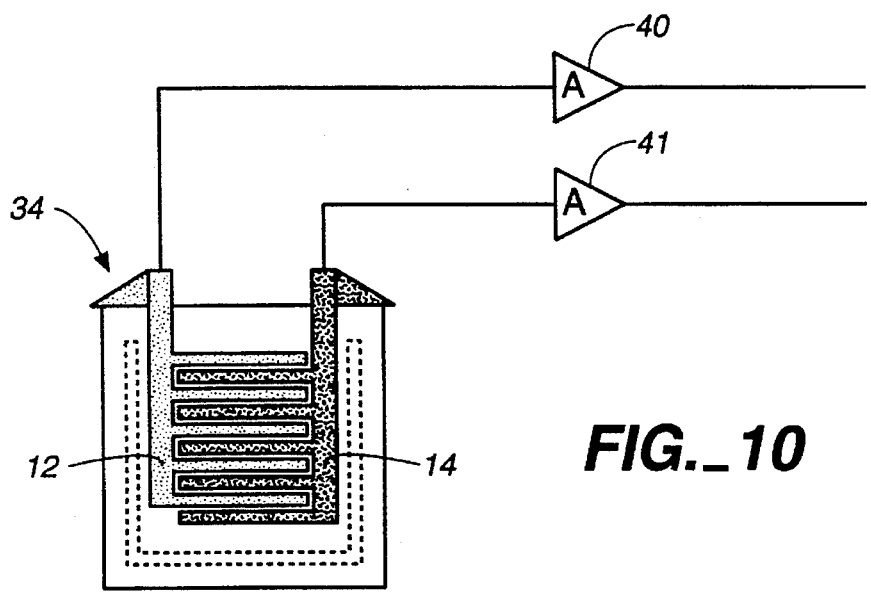
FIG._10
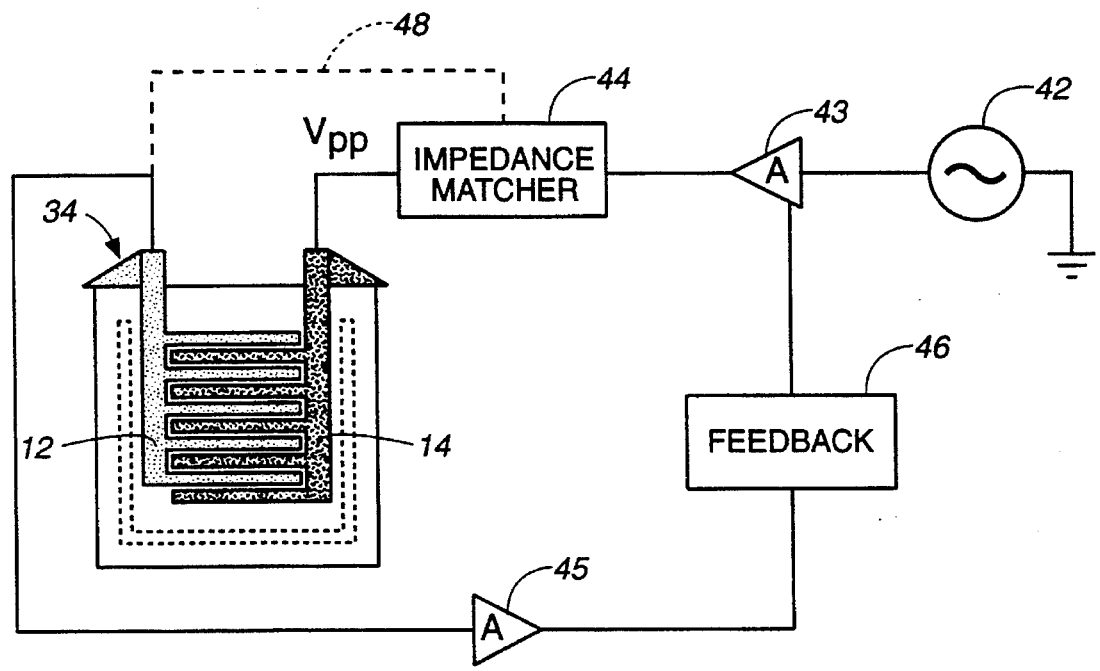
FIG._11

5,569,968

MICROFABRICATED ACOUSTIC SOURCE AND RECEIVER

STATEMENT OF RIGHTS

This invention was made with Government support under a National Science Foundation Grant awarded to the Berkeley Sensor Actuator Center (BSAC). The Government has certain rights to this invention.

This is a continuation of application Ser. No. 08/072,294, filed Jun. 4, 1993 now abandoned.

BACKGROUND OF THE INVENTION

Currently, acoustic devices such as microphones are geometrically symmetric with little internal structure. They consist of rectangular or circular plates whose motions are detected capacitively, piezoelectrically, or piezoresistively. In its operating frequency range, mechanical response of such a device is a relatively smooth function of frequency. For more complex transfer functions, electronic filters must be used.

Micromachining, on the other hand, allows the fabrication of reproducible microstructures that have complex mechanical transfer functions. Complicating the mechanical designs simplifies the electronics which, in turn, can reduce required power and increase signal-to-noise ratio. This concept may improve performance of hearing aids. Tools such as finite-element methods may be used to predict and tailor the response of a given device.

An object of the present invention is to provide a micromachined acoustic source and receiver.

Another object of the present invention is to provide a micromachined acoustic source that may be used as a microcutter, microchisel or microhammer.

Yet another object of the present invention is to provide a micromachined structure that may function as a micro-optical component in application of optical phase modulation and beam chopping.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the claims.

SUMMARY OF THE INVENTION

The present invention is directed to a microfabricated acoustic source or receiver. Acoustic encompasses both audible and ultrasonic sound. It comprises a substrate of a first material having first and second sections wherein the thickness of the first section is greater than the thickness of the second section. A membrane of a second material is supported by the substrate. The thickness of the membrane is less than that of the second section of the substrate. The microstructure further includes a means for inputting or sensing mechanical energy in the substrate and membrane. Additionally in a preselected region of the second section of the substrate, the first material has been removed to form a window section.

The micromachined structure of the present invention allows for the design of complex mechanical frequency responses. It permits signal processing to be transferred, in part, from the electrical to the mechanical domain. It reduces complexity while increasing the signal-to-noise ratio.

The micromachined structure of the present invention can exhibit a 85 decibel (dB) sound pressure level (9.7 kHz and 3 Vpp drive voltage) and 900 µV/µbar sensitivity at its resonant frequency. These resonant frequencies lie in the audio and the ultrasonic range. The device is audible to the ear and sensitive to sound in common room-like surroundings.

The structure may consist of silicon interconnected beams, plates, cantilevers, and silicon nitride thin membranes. Depositing a zinc oxide (ZnO) piezoelectric transduction film or layer allows the structure to be driven electrically. The processing involves bulk micromachining with extensive backside lithography.

The micromachining process permits fabrication of an acoustic receiver consisting of coupled oscillators that can be designed to produce a desired frequency response.

At ultrasonic frequencies, the device can be used as a microcutter, microchisel or microhammer. This may be important in the biological and medical industries for investigating and manipulating tissue, and holds the promise of better control and higher power in microcutting than other technologies such as laser cutting and ablation.

The structure can also include an optically transparent thin film. By exciting mechanical motion in this film, the optical properties of the microstructure may be changed and so affect an optical signal passing through the film. This behavior holds the promise of mass-produced micro-optical components, such as an acousto-optic phase plate.

BRIEF DESCRIPTION OF THE DRAWINGS

The accompanying drawings, which are incorporated in and constitute a part of the specification, schematically illustrate preferred embodiments of the present invention, and together with the general description given above and the detailed description of these embodiments given below, serve to explain the principles of the invention.

FIG. 1A is a schematic representation of an acoustic source and receiver in accordance with the principles of the present invention.

FIG. 1B is a view along line 1B—1B of FIG. 1A.

FIGS. 2A–2I are process flow diagrams illustrating a process for fabricating an acoustic source and receiver of the present invention.

FIGS. 3A–3D schematically represent various microstructures that may be fabricated using the process illustrated by FIGS. 2A–2I.

FIG. 4 graphically represents the sound pressure level of a microstructure of the present invention.

FIGS. 5A and 5B are graphic representations of a microphone and speaker response, respectively, for the notch structure of FIG. 3A.

FIG. 6 is a graphical representation of displacement for the notch structure of FIG. 3A.

FIG. 7 is a graphical illustration of the speaker response of the cantilever microstructure of FIG. 3B.

FIGS. 8A–8L are graphical representations of the ABAQUS derived eigenmode shapes and eigen-frequencies.

FIG. 9A schematically illustrates a microstructure of the present invention used as a surgical cutter.

FIG. 9B illustrates the elliptical motion of the microstructure of FIG. 9A.

FIG. 9C is a schematic illustration of an alternative cutting edge of the cutter of FIG. 9A.

FIG. 10 is a schematic representation of a circuit for an acoustic receiver functioning as a microphone.

FIG. 11 is a schematic representation of a circuit for an acoustic source functioning as a speaker.

DESCRIPTION OF THE PREFERRED EMBODIMENTS

The present invention is directed to a microfabricated acoustic source and receiver. This microstructure may function, for example, as a microphone or speaker at audible frequencies, and as a microcutter at ultrasonic frequencies.

The shape of the microstructure may be selected to produce a particular acoustic response. As shown in FIGS. 1A and 1B, an acoustic source and receiver 10 of the present invention may comprise interdigitated, transducer fingers 12 and 14. The fingers can be used to input mechanical energy into the microstructure. A piezoelectric ZnO layer sandwiched between aluminum planes, one of which serves as an electrical ground plane, may form the transducer fingers. By way of example, the aluminum planes may each be about 0.3 microns(μm) thick, and the ZnO film 2 microns thick.

Other transducer patterns and transduction mechanisms, other than piezoelectric, may be used. For example, the transduction mechanism may comprise a thermal stress, electrostriction, magnetostriction, or optical drive system.

Fingers 12 and 14 may function as sense or generating transducers. As will be described below in reference to FIGS. 10 and 11, if microstructure 10 functions as an acoustic receiver, for example a microphone, fingers 12 and 14 may both act as sense transducers. That is, no drive voltage (Vpp) is applied to the fingers, and stresses imparted to the microstructure will cause the transducers to generate an electrical signal. If, on the other hand, microstructure 10 functions as an output device or acoustic source, for example a speaker, a drive voltage Vpp may be applied to transducers 12 and 14. Alternatively, one transducer, for example transducer 12, may function as a sense electrode to provide feedback control, while the other transducer acts as a generating transducer to which the drive voltage is applied.

The transducer fingers may be formed on a thin silicon plate section 16 of a substrate 13 that also includes a frame or baffle section 17. The plate 16 may be between about 40 and 100 microns thick, and more preferably between about 50 and 70 microns thick.

A silicon nitride membrane or layer 15 may be formed between the fingers and plate 16. Layer 15 may be between about one and four microns thick, and more preferably about 2 microns thick. Membrane 15 may also be formed of other materials such as polysilicon, silicon dioxide or various polymers, and may comprise of sandwich materials of thin layers of many such materials.

The thickness of baffle section 17 may be between about 500 and 550 microns. The frame 17, like plate 16, may be formed of silicon. As mentioned, the frame and plate sections are part of a substrate that supports membrane 15, and transducers 12 and 14. Other materials may be used for plate 16 and frame 17. For example, quartz may be used to give the microstructure different elastic properties.

The microstructure 10 also includes a window section 18. Section 18 may be a silicon nitride film that is about 2 microns thick. The window section may be formed, as will be discussed, by removing material from preselected regions of plate section 16. As will be described, the location and pattern of the window section or sections can be selected to tailor the frequency response of the microstructure. As such, a desired frequency response may be designed for without the use of complex electronics.

The thin silicon plate configuration of microstructure 10, with very small area connecting silicon nitride, is much stronger than large-area thin membranes. Therefore, microstructure 10 can operate under very rugged conditions.

The fabrication of structure 10 may start with a four-inch silicon wafer 20. As shown in FIG. 2A, a 4000 angstrom(A) layer of low-stress silicon nitride 22 may be first deposited on the wafer in an LPCVD furnace. The nitride is patterned using lithography and plasma etching exposing the silicon areas 21 to be removed. As seen in FIG. 2B, a small square (or squares) 23 is opened on the top side for silicon membrane thickness control. The wafers are then etched in a KOH bath (FIG. 2C). The square is sized so that KOH etching ceases on the top when a certain height pyramid 26 is etched; much larger squares 24 etch on the backside concurrently. When the backside incomplete pyramid 25 encounters top pyramid 26, the transmission of light is observed and the wafer is removed from the etch bath. This method permits control of the silicon membrane thickness to within ±5 microns.

Next, as shown by FIG. 2D, a second layer of ~1.5 μm thick silicon nitride 27 is deposited over the entire wafer. Backside lithography is used to remove this silicon nitride where additional silicon 28 is to be etched (FIG. 2E). The plate structure and window section 18 (see FIGS. 1A and 1B) is then defined by removing the silicon using KOH etching (FIG. 2F). The silicon nitride (layer 15), which, as noted, may be about 2 μm, is strong enough to support the silicon substrate members (plate 16 and baffle 17) and survive further processing steps.

The next steps (FIGS. 2G–I) involve making the piezoelectric transducer fingers 12 and 14. A 3000A thick, aluminum layer with two percent silicon is sputtered on the front of the device. The sputtered aluminum is then patterned using PR lithography to form regions 29. A 2 μm thick film 30 of ZnO is then RF magnetron sputtered on the wafer. A second film 31 of aluminum is sputtered over the ZnO and is patterned by PR lithography to form the electrical ground plane. This aluminum pattern is then used as a mask to remove the exposed ZnO by etching, allowing electrical contact to the transducers to be made via aluminum regions 29.

FIGS. 3A–3D show various structures that may be fabricated using the process of FIGS. 2A–2I. These structures produce different frequency responses. The microstructures illustrated are a notch structure 32, a cantilever structure 34, and structures 36 and 38 with beams of different lengths and widths. The overall transverse dimensions "y" and "x" of the thin silicon plate 16 of these structures may be about 9 millimeter (mm) and 10 mm, respectively. The thickness of plate 16 is about 60 microns. These various designs were made to study the effect of beams and cantilevers of different lengths and widths. Transducers 12 and 14 in the shape of interdigitated fingers were used to excite very high-frequency (100 kHz and above) modes.

The window section 18 of notch structure 32, as shown in FIG. 3A, forms a simple notch in silicon plate 16 spanning two sections of the plate. The window section 18 of microstructure 34 (FIG. 3B) forms a cantilevered arrangement wherein transducers 12 and 14 are supported at one end 19 relative to plate 16. Microstructures 36 and 38 (FIGS. 3C and 3D) show beams of different lengths "l" and widths "w". For example, the lengths "l" of the beams may range from about 1 to 4 mm and the widths "w" from about 1 to 2 mm.

The following characteristics of the microstructures may be measured: sound pressure level, acoustic input/output response spectrum, and membrane deflection. Using a sound pressure level meter, the sound intensity of notch device 32 (FIG. 3A) was measured as a function of input voltage versus distance from the device. A pressure level of 85dB was measured about 1 centimeter(cm) away from the device at its 9.7 kHz resonance. The device radiated sound isotopically because the wavelength of the flexural wave is much smaller than the acoustic wavelength in air at this frequency. FIG. 4 shows the output power level in dBs. As can be seen, the pressure produces a log-like curve which, when plotted in linear pressure units, indicates a linear function of the input drive voltage Vpp.

The acoustic output as a function of frequency was also measured for notch structure 32. A microphone was placed 0.5 cm above the center of the device to measure its output when a sinusoidal signal from 4 to 50 kHz at 1 Vpp was applied to the acoustic source. Similarly, the microphone response was tested by applying a calibrated acoustic signal from an external speaker (producing signals from 4 to 20 kHz) near the acoustic receiver and measuring the signal generated. The microphone response was 900 µV/µbar at 9.4 kHz and 160 µV/µbar at 5.7 kHz. The sensitivity was higher than 40 µV/µbar in the range of 6 to 11 kHz.

The displacement of notch device 32 was also measured using a laser-amplified feedback interferometer (see FIG. 6). The resolution of the interferometer system is ~1 nanometer, well below the displacements measured. The quality factors of the resonances were found to range from 20 to 30. Since the thin silicon nitride moves as much as, if not more than, the silicon, the silicon nitride film can be used as a coupling agent between different silicon sections. The displacement at resonance reaches 100 nm (at 3 Vpp). The displacement was measured at various locations on the device in the frequency range of 10 Hz to 52 kHz to obtain an estimate of the mode shapes. The final goal, however, is to predict a response once a particular structure is given.

The notch structure 32 is complicated due to the asymmetry of the nitride window. The speaker response for the much simpler cantilever-microstructure 34 (FIG. 3B) is shown in FIG. 7. A B&K microphone was placed 1 mm away from the center of the cantilever to measure the radiated field. The dashed line represents the response in the presence of the silicon nitride window 18 connecting the silicon membrane to the frame. The heavy line shows the response with the nitride window removed. The two curves show that removing the nitride window shifted the response down by 2 to 4 kHz. Furthermore, the resonances with the nitride window are broader than those without it. This indicates that the nitride window can play a major role in determining the response of these devices: both as a coupling agent between silicon members and as a damping section, which dampens the resonance of the structure to provide a broader resonance.

To predict the response of a given microstructure, the elasticity theory specialized to layered plates coupled to a fluid such as air can be used. The cantilever structure 34 was modeled in ABAQUS, a finite-element mechanical analysis program. A 20×20 array of nodes was used with 10×10 shell elements. These shell elements consist of 9 nodes. Each shell element was modeled as a 65 µm thick silicon plate sandwiched between two 1 µm nitride membranes. The results of an eigenmode analysis appear in FIGS. 8A–8L, where the first twelve mode shapes and their respective frequencies are shown. Since the B&K microphone was located 1 mm above and near the center of device 34, with its sensitive area (~2 mm in diameter) much less than the device area, it is expected that modes that have substantial deflection at the center will contribute more to the measured response. Modes 4, 5, 8, and 12 (highlighted in FIGS. 7, 8D, BE, 8H, and 8L) have displacements that are effectively symmetric with respect to the center of the cantilever and produce large motion there in at least one of the directions. As expected, these are the same modes that match with the measured response.

The predicted frequencies are in agreement with the measured response given the resolution bandwidth of the measurement was 1 kHz. An error of about ±500 Hz exists in modes 4, 5, 8, and 12. Mode 5 has an error of about 1.1 kHz. Wrong values for material properties (such as the Poisson's ratio for silicon) being entered for the model might be responsible.

In addition to predicting the frequency, a feeling for the relative amplitude at each frequency should be obtained. At large plate wavelengths, the plate looks like a piston which pushes against a large area of air and feels the maximum resistance. This also causes the output to be isotropic as there is no preferred direction. When many wavelengths fit in the plate, the air resistance is lowered as air displaced at one point easily pushes the plate on points half wavelength away as those points displaced in the opposite direction. This lowers the effective pressure. Radiation becomes anisotropic as the wave has a preferred angle of propagation. FIGS. 8A–8L show the mode shapes for each mode. The acoustic wavelengths in each direction of the plate can be estimated. As can be seen, modes 4 (FIG. 8D) and 5 (FIG. 8F) radiate well because they are essentially piston-like, while modes 8 (FIG. 8H) and 12 (FIG. 8L) do not radiate well because they have many maximums and minimums and are not piston-like.

A micromachined acoustic source and receiver has been described that can produce 85dB sound pressure level (at 7 kHz and 3 Vpp drive) and 900 µV/µbar sensitivity at its resonant frequency. These frequencies lie in the acoustic and low ultrasonic ranges. A cantilever microstructure in a finite-element analysis using shell elements was modeled, which confirms that the elastic shell theory can be used to design a response.

The acoustic source and receiver shows promise in hearing aids and other applications where a compact acoustic source is required. A combination of speaker and microphone on one chip, integrated with other electronics, can be used to measure speed using the doppler effect, or can be used to measure distance. For hearing aid applications, the frequency response can be designed into the mechanical microstructure. Thus, a hearing aid custom-tailored for an individual may be fabricated. Furthermore, the transduction system described herein is mainly capacitive and therefore consumes very little power. This gives the opportunity to make the electronics simpler to reduce the power budget. In addition, unlike other micromachined microphone structures made of thin diaphragms and membranes, this device is made of a relatively thick silicon plate 16 supported by very thin silicon nitride membranes (windows) that can withstand harsh environments.

At ultrasonic frequencies, plate modes in the structure can be excited. Thus, an open-ended plate 50 can be used as a cutter (see FIG. 9A). The cutter may be fabricated as described above and include interdigitated transducers 52 and 54. The cutter may include an angled cutting edge 55. The angle 8 of the cutting edge can be about 57.3°. An ultrasonic, flexure wave generated at one end of the cutter will travel to cutting end 55, producing an elliptical motion 58 as shown in FIG. 9B. This motion can be used to cut soft materials such as tissue. Since the zeroth order antisymmetric Lamb mode has a phase velocity less than that of sound in water, acoustic energy will be trapped in the plate while that motion cuts at the cutting end. An alternate cutting edge 56 for the microcutter is shown in FIG. 9C. This edge incorporates a beak-like configuration.

As a cutter, the present invention holds the promise of cutting biological tissue in diseases like cataracts (most-performed operation in the United States) and clogged arteries. Splicing cells and cutting tissue precisely can be very useful technologies for the biology industry.

The use of a microstructure, in this example cantilever structure 34, as an acoustic receiver, for instance a microphone, is shown in FIG. 10. The transducers 12 and 14 both act as sense electrodes whose output is applied to amplifiers 40 and 41, respectively.

A circuit for an acoustic source is shown in FIG. 11. The source, for example, may function as a speaker or cutter. A voltage source 42 is connected to an impedance matcher 44 through an amplifier 43. The output of the impedance matcher, drive voltage Vpp, is applied to generating transducer 14. Transducer 12 acts as a sense transducer for a feedback loop including amplifier 45 and feedback circuitry 46. The feedback loop can control the frequency response and the amplitude of motion of the microstructure.

Alternatively, as shown by dashed line 48 in FIG. 11, both transducers 12 and 14 may act as generating transducers when the microstructure functions as a source. In this embodiment, the feedback loop would be eliminated.

It is also possible to connect the microstructure of the present invention in a circuit so it functions both as a source and a receiver. That is, for example, it may act as both a microphone and speaker at audible frequencies.

As discussed, the fabrication process allows for the fabrication of thin transparent film sandwiches that can act as windows 18 (see FIGS. 1A–1B). When a mechanical vibration (bending) is applied to the microstructure, stresses may cause a change in transmittance and index of refraction of the thin film. A change in index of refraction and absorption properties (elasto-optic properties) of the window section can be used to modulate and/or deflect light.

As an optical device, the microstructure of the present invention can provide inexpensive phase plates in optical systems which are shrinking in size due to requirements of larger number of optical components in a small package and portability of such systems.

The present invention has been described in terms of a number of embodiments. The invention, however, is not limited to the embodiments depicted and described. Rather, the scope of the invention is defined by the appended claims.

What is claimed is:

1. A microfabricated acoustic source or receiver structure, comprising:

a substrate of a first material, said substrate having first and second sections wherein said first section is thicker than said second section;

a membrane of a second material disposed on said substrate over said first and second sections;

means, mechanically coupled to said membrane, for inputting or sensing mechanical energy in said membrane and said substrate; and wherein said second section of said substrate includes a plate shaped to produce a predetermined acoustic response, said plate shaped by removing said first material from a preselected region of said second section of said substrate exposing said membrane, said preselected region having a lateral extent less than a lateral extent of said second section.

2. The structure of claim 1 wherein said first material is silicon.

3. The structure of claim 1 wherein said membrane has elasto-optic properties.

4. The structure of claim 1 wherein said inputting means includes a piezoelectric transducer.

5. The structure of claim 4 wherein said transducer means includes a zinc oxide layer and two layers of a conductive material, said zinc oxide layer disposed between said layers of a conductive material.

6. The structure of claim 1 wherein the thickness of said first section is between about 500 and 550 microns.

7. The structure of claim 6 wherein the thickness of said second section is between about 40 and 100 microns.

8. The structure of claim 6 wherein the thickness of said second section is between about 50 and 70 microns.

9. The structure of claim 1 wherein the thickness of said membrane is between about one and four microns.

10. The structure of claim 9 wherein the thickness of said membrane is about two microns.

11. A microfabricated acoustic source structure, comprising:

a substrate of a first material, said substrate having first and second sections wherein said first section is thicker than said second section;

a membrane of a second material disposed on said substrate over said first and second sections;

transducer means mechanically coupled to said membrane;

means for supplying electrical power to said transducer means to cause a flexural wave action in said second section of said substrate; and wherein said second section of said substrate includes a plate shaped to produce a predetermined acoustic response, said plate shaped by removing said first material from a preselected region of said second section of said substrate exposing said membrane, a lateral extent of said preselected region being less than a lateral extent of said second section.

12. The structure of claim 11 wherein said first material is silicon.

13. The structure of claim 11 wherein said second material is silicon nitride.

14. The structure of claim 11 wherein said transducer means includes a piezoelectric film.

15. The structure of claim 11 wherein the thickness of said first section is between about 500 and 550 microns.

16. The structure of claim 15 wherein the thickness of said second section is between about 40 and 100 microns.

17. The structure of claim 11 wherein the thickness of said membrane is between about one and four microns.

18. The structure of claim 17 wherein the thickness of said membrane is about two microns.

19. The structure of claim 11 wherein said transducer means includes a plurality of parallel finger elements of conductive material connected to said electrical power supplying means.

20. The structure of claim 11 wherein said transducer means includes first and second conductive elements wherein said first conductive element is connected to said electrical power supplying means and said second conductive element is connected in a feedback loop for controlling frequency response of the structure.

21. A microfabricated acoustic receiver structure, comprising:

a substrate of a first material, said substrate having first and second sections wherein said first section is thicker than said second section;

a membrane of a second material disposed on said substrate over said first and second sections;

transducer means mechanically coupled to said substrate for sensing mechanical vibration in said second section to produce an electrical signal; and wherein said second section comprises a plate shaped to produce a predetermined acoustic response, said plate shaped by removing said first material from a preselected region of said second section of said substrate exposing said membrane, said preselected region having a lateral extent less than a lateral extent of said second section.

22. The structure of claim 21 wherein said first material is silicon.

23. The structure of claim 21 wherein said second material is silicon nitride.

24. The structure of claim 21 wherein said transducer means includes a piezoelectric film.

25. The structure of claim 21 wherein the thickness of said first section is between about 500 and 550 microns.

26. The structure of claim 25 wherein the thickness of said second section is between about 40 and 100 microns.

27. The structure of claim 21 wherein the thickness of said membrane is between about one and four microns.

28. The structure of claim 21 wherein said transducer means is connected to an amplification means for amplifying the electrical signal.

29. A microfabricated acoustic receiver structure, comprising:

a substrate of a first material, said substrate having first and second sections wherein said first section is thicker than said second sections;

transducer means mechanically coupled to said substrate for sensing mechanical vibration in said second section to produce an electrical signal; and wherein said second section has a preselected region from which said first material has been removed, said preselected region having a lateral extent less than a lateral extent of said second section, said second section including a plate shaped to produce a predetermined acoustic response and said preselected region defines a notch structure that does not enclose said transducer means.

30. The structure of claim 29 wherein said notch structure includes at least one beam.

31. A microfabricated acoustic receiver structure, comprising:

a substrate of a first material, said substrate having first and second sections wherein said first section is thicker than said second section;

transducer means mechanically coupled to said substrate for sensing mechanical vibration in said second section to produce an electrical signal; and wherein said second section has a preselected region from which said first material has been removed, said preselected region having a lateral extent less than a lateral extent of said second section, said second section including a plate shaped to produce a predetermined acoustic response and said preselected region defines a cantilever structure that encloses at least part of said transducer means.

32. The structure of claim 31 wherein said cantilever structure includes at least one beam.

33. The structure of claim 11 wherein said plate has an open end.

34. The structure of claim 33 wherein said open end has an angled cutting edge.

35. The structure of claim 34 wherein said open end has a beak-like configuration.

36. The structure of claim 1 wherein said second material is silicon nitride.

37. A method for producing acoustic signals, comprising:

providing an acoustic source including a substrate of a first material, said substrate having first and second sections wherein said first section is thicker than said second section; means, a membrane disposed on said substrate over said first and second sections, means, mechanically coupled to said membrane, for inputting mechanical energy in said substrate; and wherein said second section of said substrate includes a plate shaped to produce a predetermined acoustic response, said plate shaped by removing said first material from a preselected region of said second section of said substrate exposing said membrane, said preselected region having a lateral extent less than a lateral extent of said second section; and activating said means for inputting mechanical energy in said substrate.

38. A method for receiving acoustic signals, comprising:

providing an acoustic receiver including a substrate of a first material, said substrate having first and second sections wherein said first section is thicker than said second section; a membrane disposed on said substrate over said first and second sections; means, mechanically coupled to said substrate, for sensing mechanical energy in said substrate; and wherein said second section of said substrate includes a plate shaped to produce a predetermined acoustic response, said plate shaped by removing said first material from a preselected region of said second section of said substrate exposing said membrane, said preselected region having a lateral extent less than a lateral extent of said second section; and using said means for sensing mechanical energy in said substrate to sense said acoustic signals.

39. A microfabricated acoustic source or receiver structure, comprising:

a substrate of a first material, said substrate having first and second sections wherein said first section is thicker than said second section;

a membrane of a second material disposed on said substrate over said first and second sections;

means, mechanically coupled to said membrane, for inputting or sensing mechanical energy in said membrane and said substrate; and wherein said second section of said substrate includes a plate shaped to produce a predetermined acoustic response, said plate shaped by removing said first material from a preselected region of said second section of said substrate exposing said membrane.

* * * * *